United States Patent
Kimmel

[11] Patent Number: 5,890,487
[45] Date of Patent: Apr. 6, 1999

[54] CORN FILLED HEATING PAD

[76] Inventor: Reneé S. Kimmel, 205 E. Dimond Blvd. #520, Anchorage, Ak. 99515

[21] Appl. No.: 137,221
[22] Filed: Aug. 19, 1998

Related U.S. Application Data

[60] Provisional application No. 60/057,345, Aug. 26, 1997.
[51] Int. Cl.[6] .................................................. A61G 15/00
[52] U.S. Cl. ............................................ 128/845; 607/114
[58] Field of Search ..................................... 128/845, 846, 128/878, 879, 882; 607/108, 114

[56] References Cited

U.S. PATENT DOCUMENTS 4,886,063  12/1989  Crews ...................................... 607/114
5,184,613  2/1993   Mintz ...................................... 128/402
5,300,104  4/1994   Gaudreault .............................. 607/114
5,395,399  3/1995   Rosewald ................................ 107/108

Primary Examiner—Michael A. Brown
Attorney, Agent, or Firm—Michael J. Tavella

[57] ABSTRACT

A generally flat, fabric bag to hold a quantity of dried Indian corn. The Indian corn can be heated in a microwave oven. Once heated, the corn holds a large quantity of heat and can produce heating for several hours. The corn can also be cooled in a freezer to produce hours of cooling therapy, if desired. The fabric bag not only holds the corn, but also acts a thermal shield to protect the user from excessive temperatures produced by the corn.

10 Claims, 12 Drawing Sheets

CORN FILLED HEATING PAD

CROSS REFERENCE TO RELATED APPLICATIONS

Provisional application 60/057,345, filed Aug. 26, 1997.

STATEMENT REGARDING FEDERALLY SPONSORED RESEARCH AND DEVELOPMENT

Not Applicable

BACKGROUND OF THE INVENTION

1. Field of the Invention

This invention relates to heating pads and particularly to heating pads using a fungible heating element.

2. Description of Related Art

Heating pads have been used for years to warm the body during cold weather and to help soothe sore muscles or joints after heavy work or exercise. Ice has also been used as a way of preventing inflammation and swelling of injured areas of a body. Recent developments in gel technology have produced a gel pack that can be heated in a microwave oven, or cooled in a freezer. This type of pack, however, must be wrapped in a towel before use, as direct contact with the skin can cause injury to the user. Moreover, the gel packs do not provide lasting heat. Finally, the gel packs can crack or break open. Once the plastic container has failed, the gel pack is useless as the gel cannot be contained.

As mentioned above, the gel packs must be used with a towel or other covering to prevent injury. It is also a good idea to use some type of wrap to place and hold the gel pack in place. A gel pack by itself, for example, cannot be wrapped around a knee or ankle without an external wrap or band to secure it in place.

Besides gel packs, traditional heating pads are also available. These pads are typically powered by electricity are not portable. Moreover, these pads cannot be chilled to provide cold therapy if such therapy is needed.

BRIEF SUMMARY OF THE INVENTION

The instant invention overcomes these problems. It uses a generally flat, fabric bag to hold a quantity of dried Indian corn. The Indian corn can be heated in a microwave oven. Once heated, the corn holds a large quantity of heat and can produce heating for several hours. The corn can also be cooled in a freezer to produce hours of cooling therapy, if desired. The fabric bag not only holds the corn, but also acts a thermal shield to protect the user from excessive temperatures produced by the corn.

Another advantage of the fabric bags is that they can be made in a variety of styles, thereby increasing the effectiveness of the therapy. For example, one style fits over a user's shoulders and neck. Another can be worn around the waist or the back. Another can be worn around the knee, ankle or elbow. Another model can be worn as a mitt to warm a user's hands.

It is an object of this invention to provide a heating and cooling pad that can be worn on a person to cover an affected area of the person's body to direct heat or cold into the affected area.

It is another object of this invention to provide a heating and cooling pad that automatically insulates the source of heat or cold from direct contact with a user's skin.

DETAILED DESCRIPTION OF THE INVENTION

Figure 1:
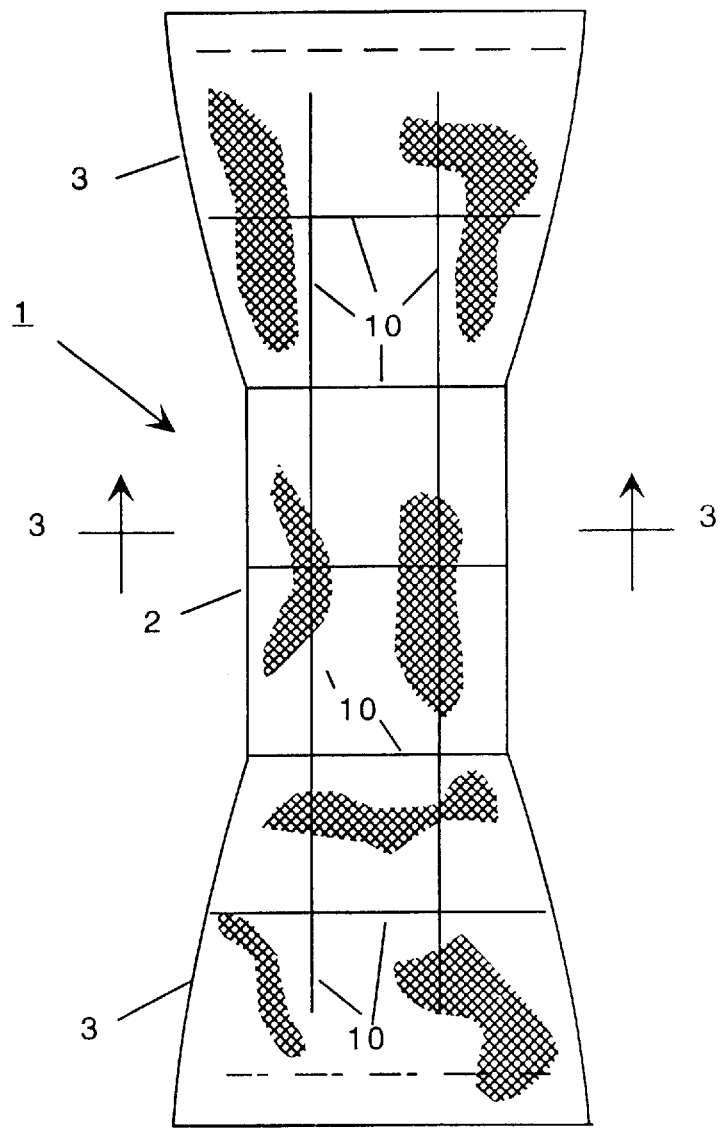
FIG. 1 is a side view of the first embodiment of the invention.
Figure 2:
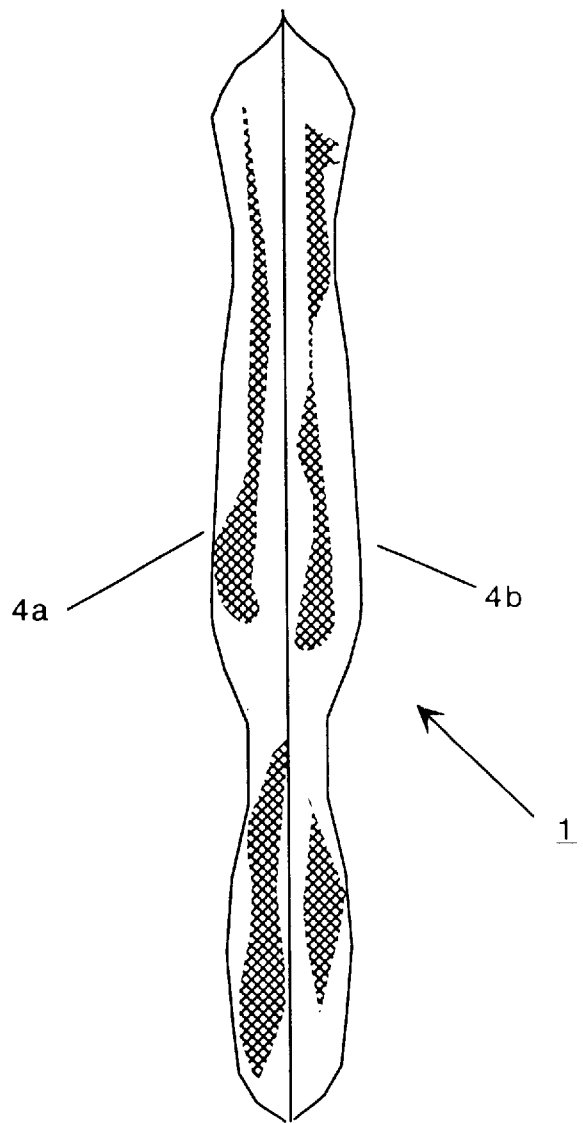
FIG. 2 is a top view of the first embodiment of the invention.

Referring now to FIG. 1, the first embodiment 1 of my heating pad is shown. In this embodiment, the pad 1 has a narrow center portion 2 and two flared ends 3 as shown. FIG. 2 shows a top view of the pad 1. The pad is formed by sewing two pieces of cloth 4a and 4b together to form a closed bag 1. The bag 1 is then filled with corn 6. See, FIG. 3. In the preferred embodiment, this corn is Indian field corn having a low moisture content. Complete details for the manufacturing process are described below.

The corn is first, cleaned and, if desired, scented. Then it is placed in the bag 1 and then the bag is closed with a set of stitches. To keep the corn spread throughout the bag, a number of baffle stitches 10 are used. These stitch lines 10 divide the bag 1 into sections that hold a uniform quantity of corn 6.

Figure 3:
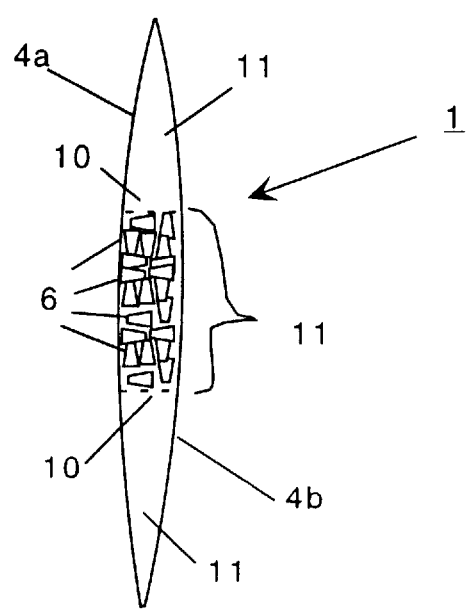
FIG. 3 is a cross-sectional view of the first embodiment of the invention taken along the lines 3—3 of FIG. 1.

Referring to FIG. 3, details of the baffle stitches 10 and the bag 1 construction are shown. Here, an inner section formed by the baffle stitches 10 are shown. Corn 6 is shown in one of the pockets 11, but is omitted from others to show the structure of the pad. In practice, corn 6 fills all the pockets 11.

The first embodiment 1 is used primarily over the shoulders. The wide end portions drape over the tops of the shoulders. The long center portion runs along the upper back or neck. Of course, the pad can be used in any other way on the body.

The remaining embodiments are made in the same way as the first embodiment. The only differences are the overall shape of the pads and the fittings that are provided.

Figure 4:
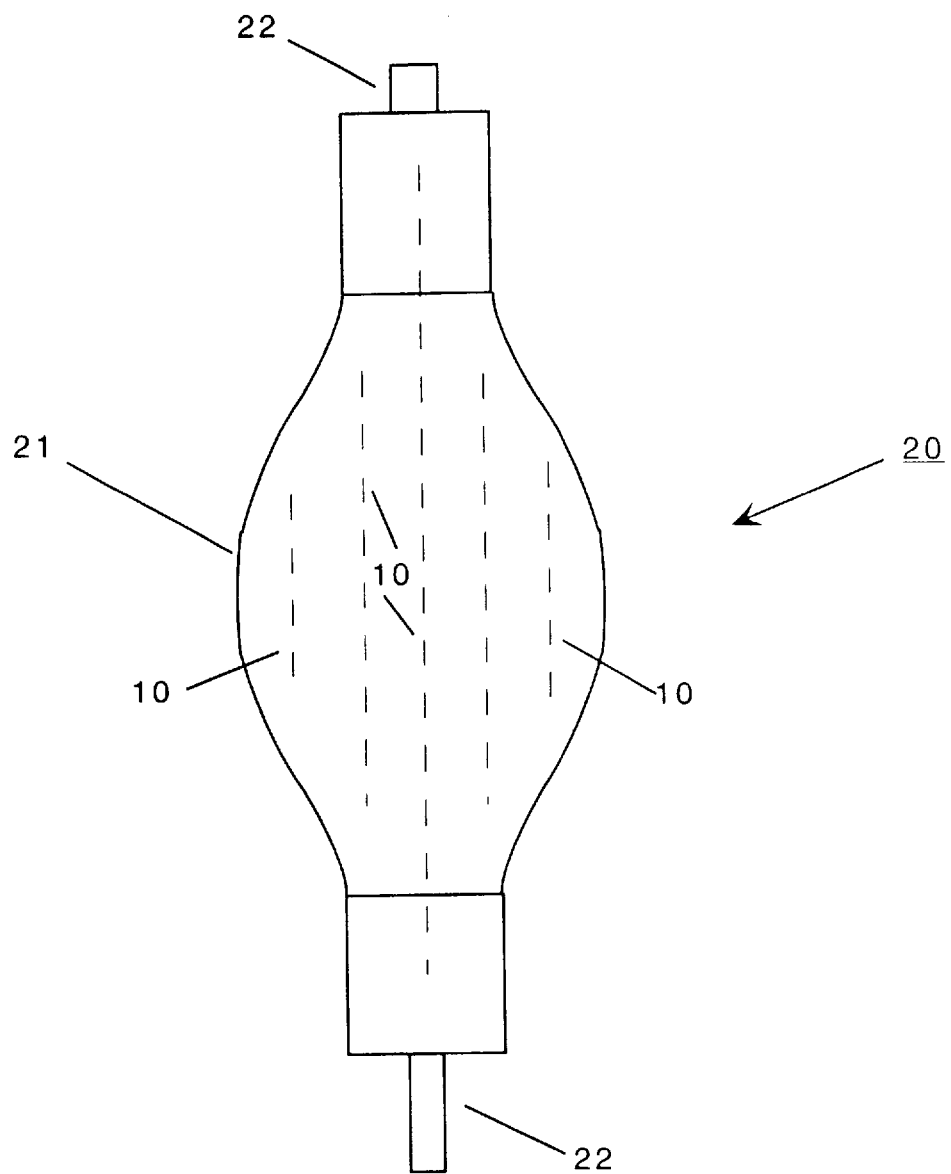
FIG. 4 is a side view of the second embodiment of the invention.
Figure 5:
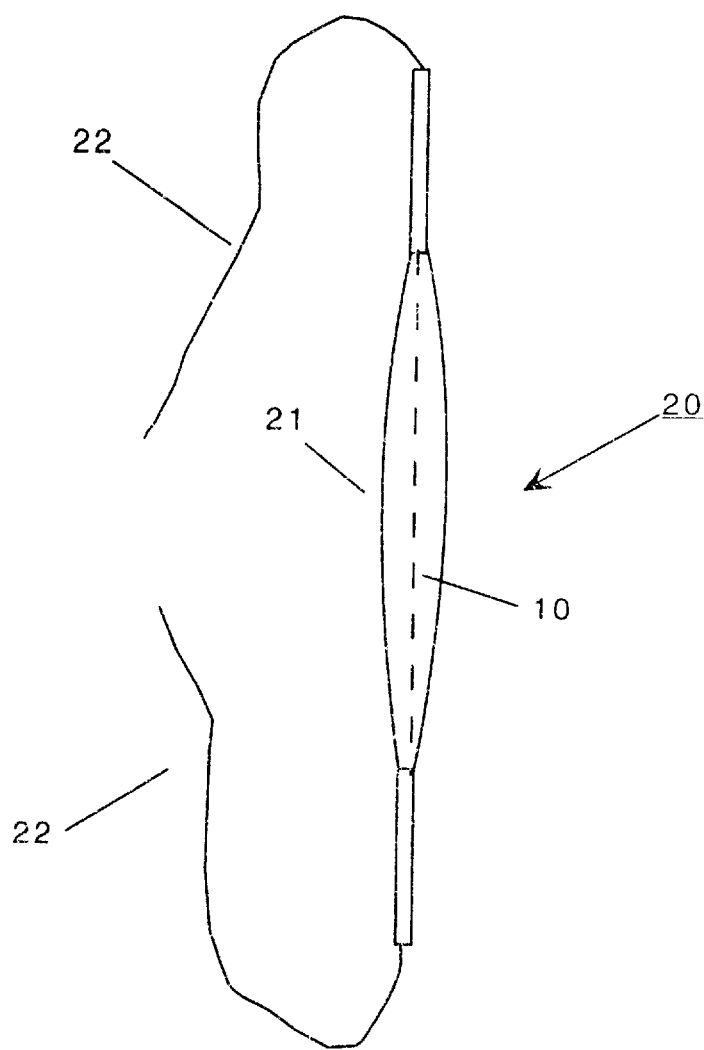
FIG. 5 is a top view of the second embodiment of the invention.

FIGS. 4 and 5 show the second embodiment 20. This embodiment 20 is intended for use primarily around the waist. In this way, heat can be applied to the lower back or abdomen. This embodiment 20 has a center pad portion 21, that is made in the same manner as the first embodiment 1, except that the second embodiment 20 has an ovular shape. Two straps 22 are provided to secure the pad around the body. In the preferred embodiment, the straps 22 are covered with VELCRO, a hook and loop type fastener. The hook portion is placed one of the two straps, and the loop portion is placed on the other. Of course, any other type of fastening system may be used as well.

Figure 6:
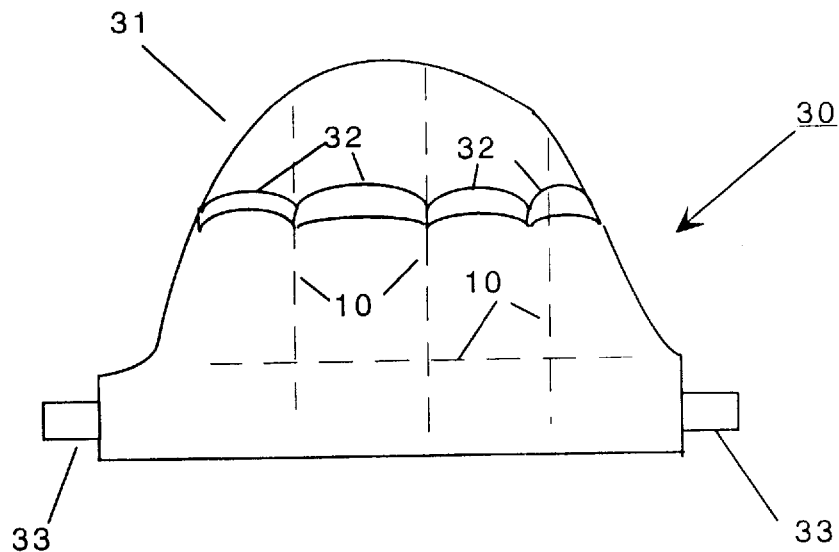
FIG. 6 is a front view of the third embodiment of the invention.
Figure 7:
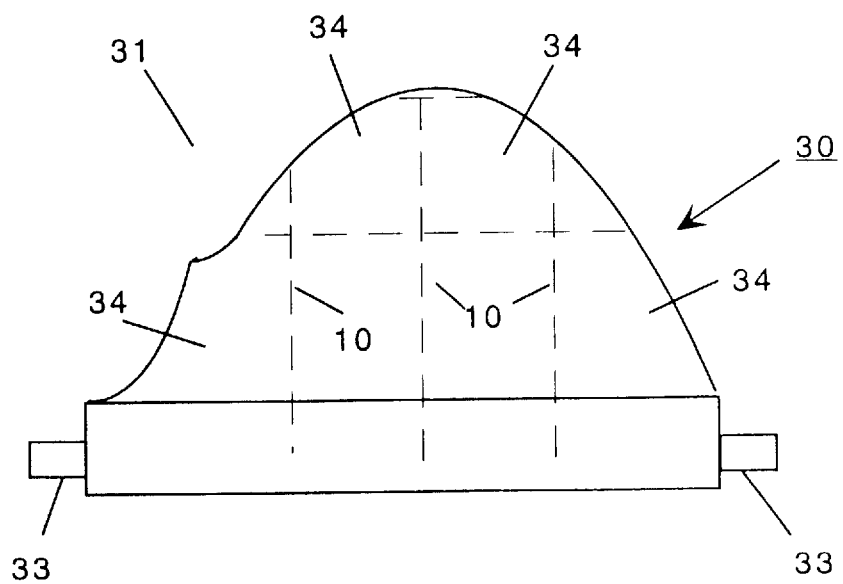
FIG. 7 is a rear view of the third embodiment of the invention.

FIGS. 6 and 7 show the third embodiment 30. In this embodiment, the pad 31 is formed into a mitt 30 that covers the back of a hand. A number of loops 32 are attached near the top front of the mitt 30. See FIG. 6. These loops 32 hold a user's fingers. The base of the mitt 30 has straps 33 covered with VELCRO that are used to close the mitt about the user's wrist. The mitt 30 is filled with corn as discussed below. However, unlike the other models, the mitt has separate compartments 34 for the corn that are not baffled. Stitches 10 are used to connect the separate compartments 34. This separation of compartments allows the mitt to work best in a more mobile and flexible application.

Figure 8:
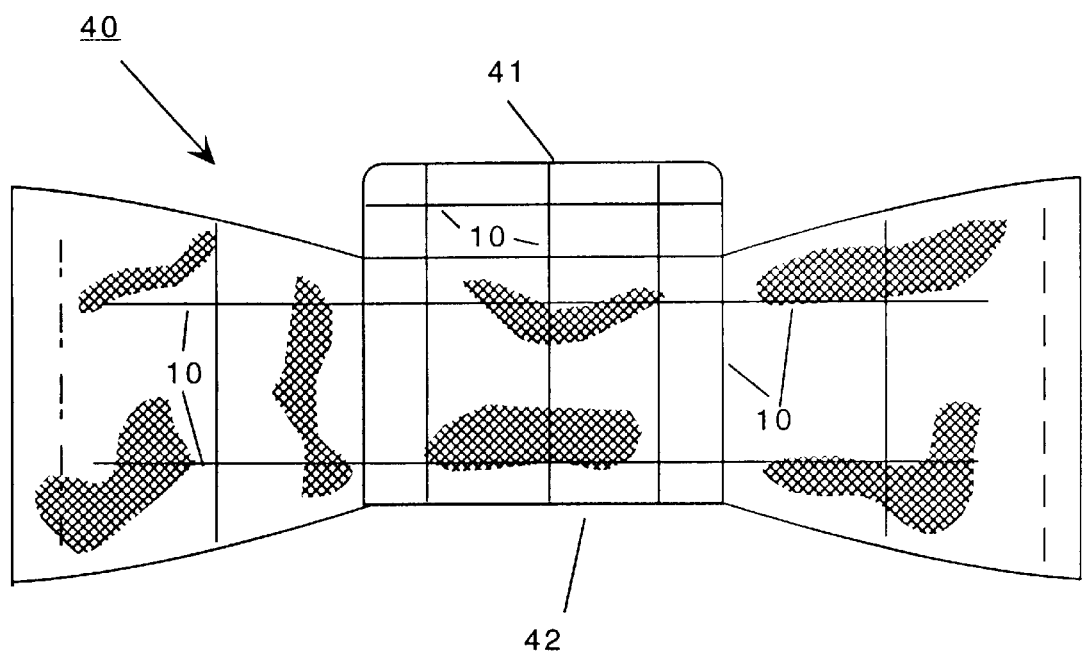
FIG. 8 is a side view of a fourth embodiment of the invention.
Figure 9:
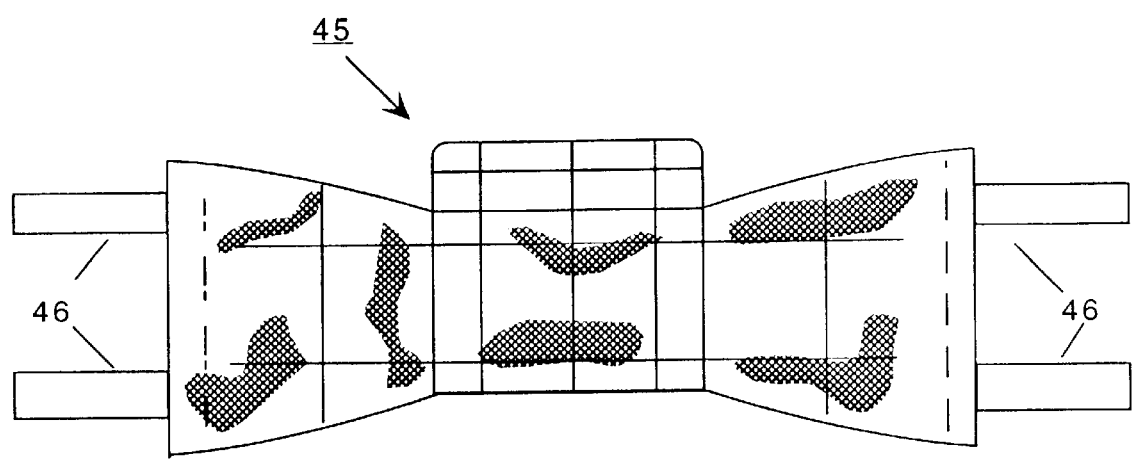
FIG. 9 is a side view of a fifth embodiment of the invention.

FIGS. 8 and 9 are modifications of the first embodiment. In the embodiment of FIG. 8, 40, a collar 41 is attached to one edge of the bag 42 as shown. This collar is filled with corn and baffled stitched, as discussed below. All other aspects of this model are the same as those of the first embodiment.

FIG. 9 is a further modification 45, in which two pairs of VELCRO straps 46 are provided as shown. These straps allow the unit to be secured around a user's waist, for example, to provide heating comfort to the lower back. Of course, the unit can be placed anywhere else as desired. Other than the addition of the VELCRO straps 46, all aspects of this model are identical to those of FIG. 8.

Figure 10:
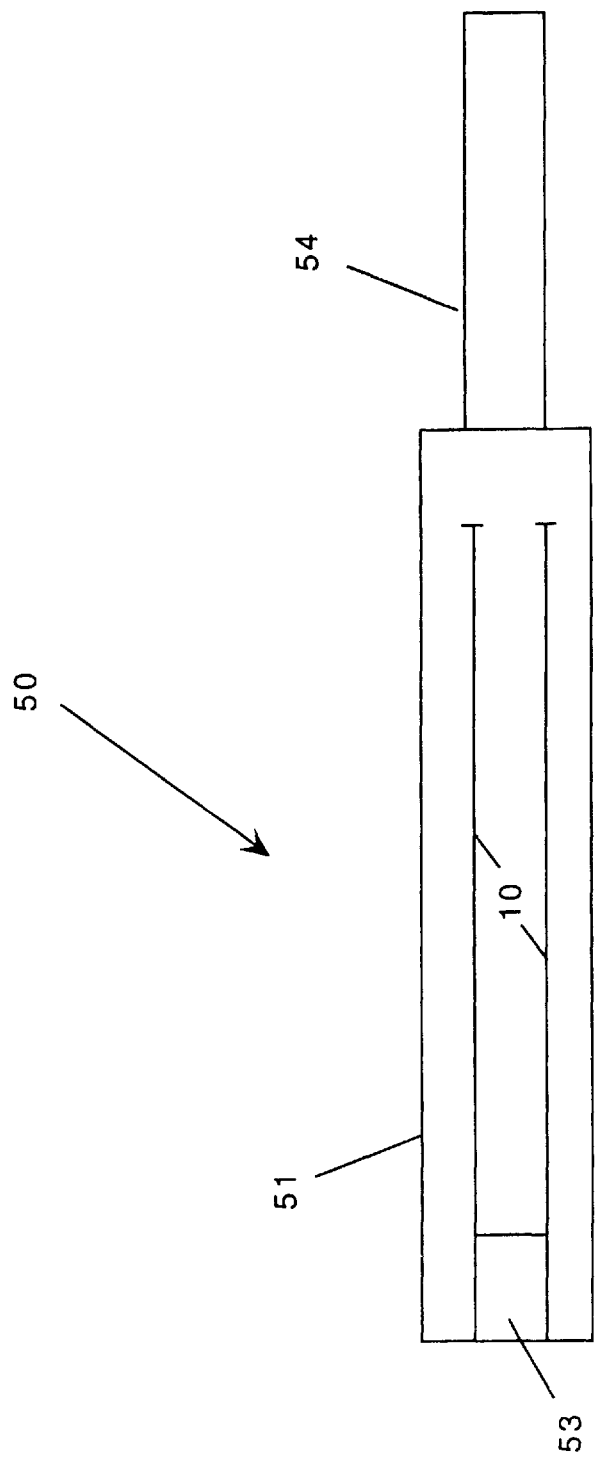
FIG. 10 is a side view of a sixth embodiment of the invention.

FIG. 10 shows another embodiment 50. In this embodiment, the bag 51 is shaped to be long and thin. The bag 51, when heated or cooled can be wrapped around a user's head to provide relief to the forehead area. This model can also be worn around the neck to provide relief for that area also. A VELCRO patch 53 and a VELCRO strap 54 are provided as shown to attach the bag 50 to a user's neck or head.

Figure 11:
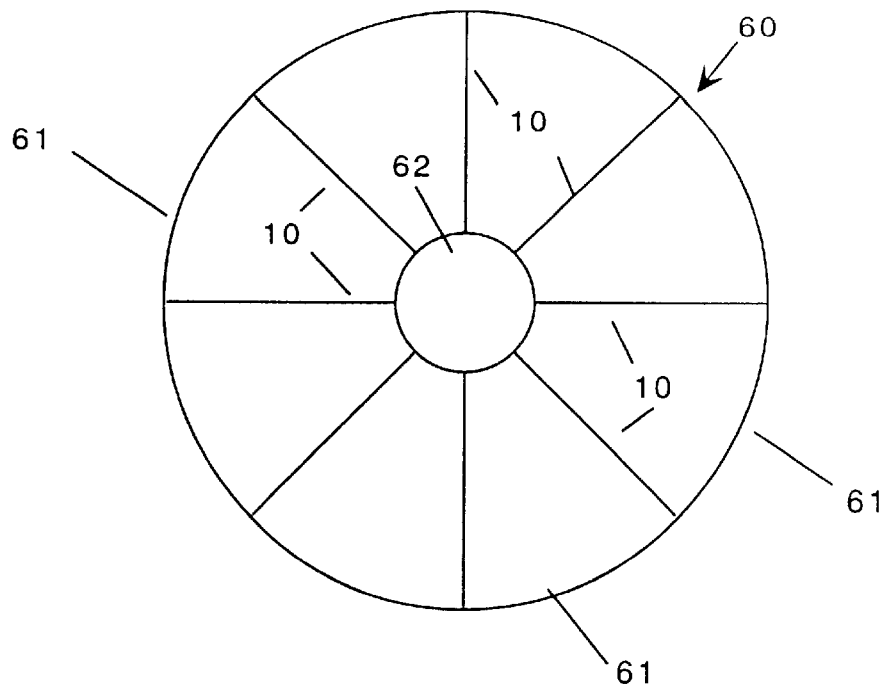
FIG. 11 is a side view of a seventh embodiment of the invention.
Figure 12:
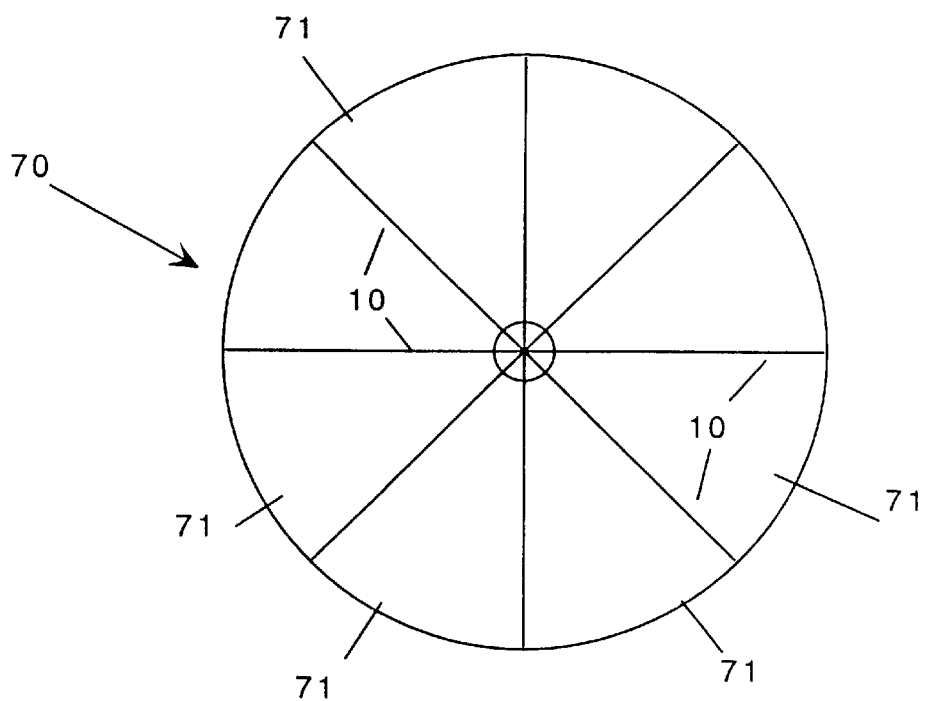
FIG. 12 is a side view of a eighth embodiment of the invention.

FIGS. 11 and 12 are two specialty units. FIG. 11 is a mastitis pad 60, used for relief of sore breasts by lactating mothers. This pad has a number of filled sections 61 that are connected together. Once they sections 61 are connected, they form an open center 62 as shown. The open center accommodates a women's nipple when the pad is worn. The sections 61 are made and filled separately, as in the case of the mitt. These sections are then joined to form the pad 60 using stitches 10 as shown.

FIG. 12 is a mastectomy pad 70 that can be worn to relieve pain caused by that procedure. Unlike the mastitis pad, this pad has no center opening. This pad is made up of a number of separate sections 71 that are made the same as those of the pad 60. These sections are then joined by stitches 10 to form the pad 70.

Figure 13:
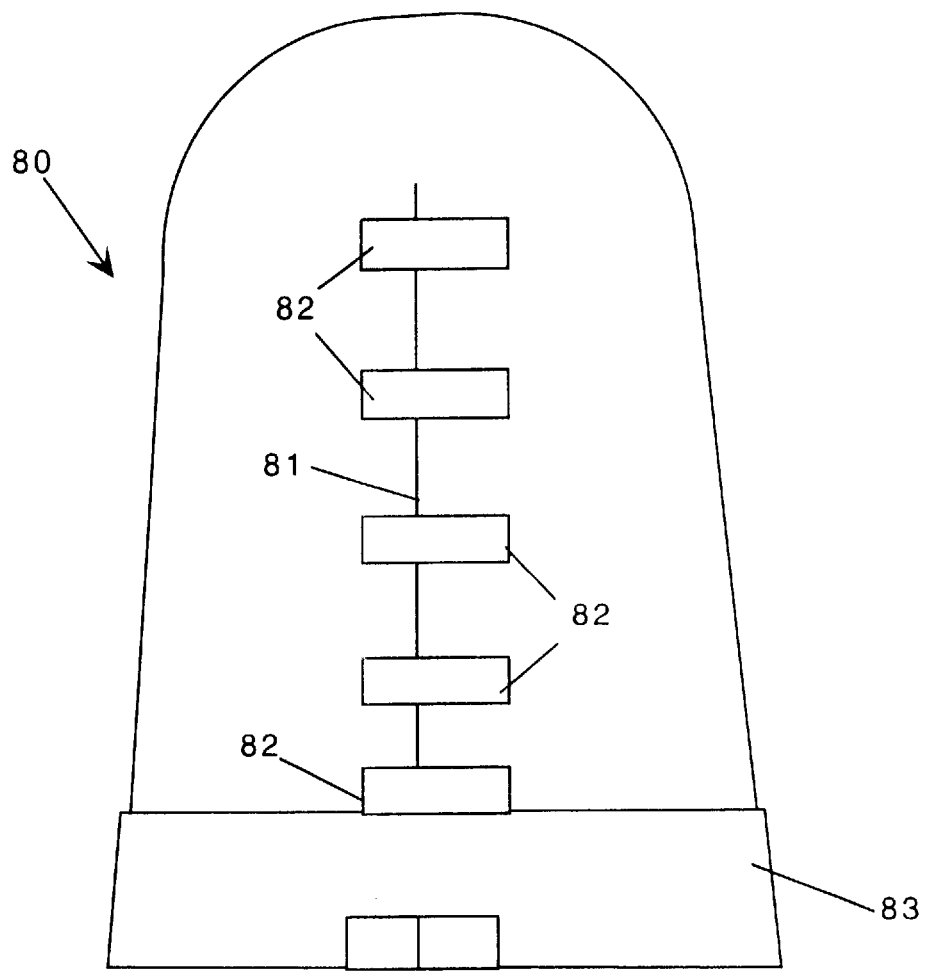
FIG. 13 is a side view of a ninth embodiment of the invention.

FIG. 13 is yet another specialized pad 80. This unit is used to provide comfort for amputees. The unit 80 can be worn on either arm or leg stumps. The unit is generally cylindrical and has an open seam 81 as shown. Several strips 82 of VELCRO are provided as shown to secure the pad 80 to the body. At the bottom of the pad is a length of elastic cuff fabric 83 that makes for a smooth and comfortable transition for the user. The cuff fabric 83 also acts to hold the pad 80 on the body.

The construction techniques are similar for all embodiments, with some variations as discussed above. The fabric is cut using template patterns. Templates are formed for each embodiment. In the preferred embodiment, the pads are made of two types of fabric. The top panel is typically cut from all cotton material. The bottom panel is cut from either a chamois cloth or a doe suede cloth. All cloth is fire resistant.

The top and bottom panels are matched face in and serged together, leaving one end of the device open for filling. Baffles are added, as discussed above, for those units that require uniform distribution and fluidity of corn movement.

Units like the third embodiment (the mitt) are made in shaped sections without baffles. This separates the pockets of corn and ensures an even distribution of corn throughout the pad.

The corn 6 is decobbed and stored as kernels in bins. The corn is then tumbled in a screen tumbler to shake off loose dust and dirt. In the preferred embodiment, each load of corn is tumbled for two hours. Fragrance oils may be added to the shaker during the tumbling process, if such scenting of the corn is desired. The tumbled corn is then stored in bins awaiting the filling process.

Figure 14:
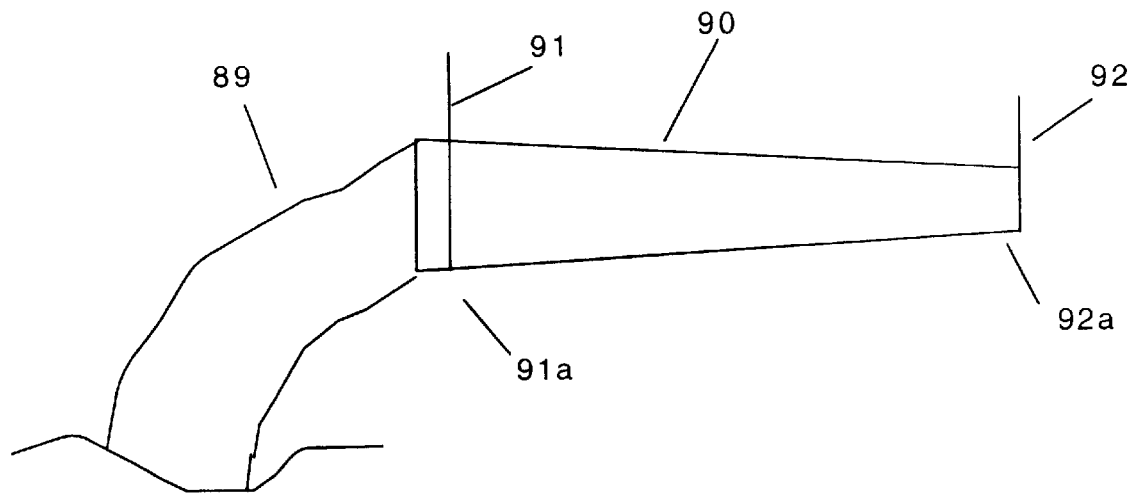
FIG. 14 is a side detail view of a filling nozzle.
Figure 15:
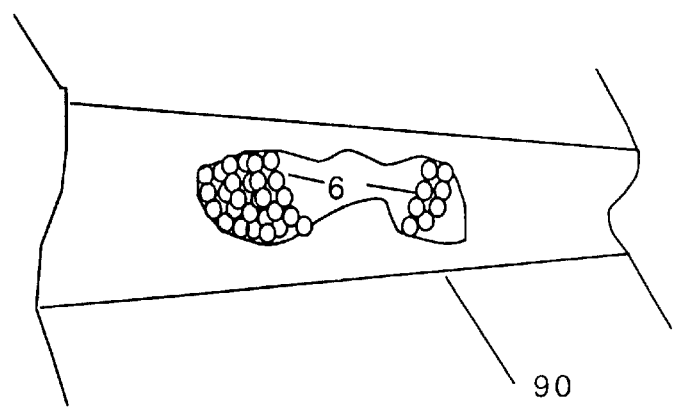
FIG. 15 is a cutaway view of the filling nozzle filled with corn.

The pads are filled using a hose 89 and a thirty inch long pipe nozzle 90. See FIGS. 14 and 15. The nozzle 90 has two sliding gates 91 and 92 that ensure constant filling. The nozzle 90 has an inlet side 91a and an outlet side 92a. The gate on the inlet side, 91 is opened, and the nozzle is allowed to be filled with a quantity of corn 6. See, FIG. 15. The inlet gate 91 is then closed. The nozzle is then placed into the pad and the outlet nozzle 92 is opened, allowing the pad to be filled with the corn 6. Final weighing is done on a scale to ensure a uniform product.

Finally, the filed bag is sewn closed, labels and, where appropriate, the VELCRO straps are added. Finally, each bag is inspected and packaged.

In all cases, the pads are heated in a microwave oven for about two minutes. This provides adequate energy to heat the pad for up to two hours. If a cool pad is desired, the pad can be placed in a freezer for as long as desired and worn as a cooling pad. The corn maintains a cool temperature for several hours.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. A heating pad comprising:
    a) a first wall;
    b) a second wall, having the same configuration as the first wall, and being in alignment therewith;
    c) means for fixedly connecting said first wall and said second wall together, thereby forming a bag structure;
    d) a quantity of dry corn, placed within said bag structure; and
    e) means for restricting the movement of said quantity of dry corn within said bag structure.

2. The heating pad of claim 1 wherein said first wall and said second wall have ends, and further wherein said ends are flared.

3. The heating pad of claim 1 wherein the first and second walls have a generally ovular shape.

4. The heating pad of claim 3 further comprising a means for securing said heating pad around a person's body.

5. The heating pad of claim 4 wherein the means for securing said heating pad comprise a pair of straps; and a means for securing said pair of straps together.

6. The heating pad of claim 5 wherein the means for securing said pair of straps together further includes a means for adjusting the length of said pair of straps.

7. The heating pad of claim 6 wherein said first and second walls have a center, and further, wherein said first and second walls have a hole formed in the center of said first and second walls.

8. The heating pad of claim 1 wherein the first and second walls are circular for fitting over a breast of a woman.

9. A heating pad comprising
   a) an outer wall, being generally shaped in a form of an open hand;
   b) an inner wall, having the same shape and configuration as the outer wall portion and being in alignment therewith;
   c) means for fixedly connecting said inner wall and said outer wall together, thereby forming a bag structure, capable of fitting on the back of a hand;
   d) a quantity of dry corn, placed within said bag structure;
   e) means for restricting the movement of said quantity of dry corn within said bag structure;
   f) a means for securing said heating pad on a person's fingers; and
   g) a means for securing said heating pad about a person's wrist.

10. A heating pad comprising:
   a) a generally cylindrical body, having an inside wall and an outside wall, a closed top and an open bottom, wherein said inside wall and said outside wall are fastened together, thereby forming a cylinderical bag, and further wherein said cylinderical bag has an open seam;
   b) means for temporarily closing said open seam, fixedly attached to said outside wall of said generally cylinderical body;
   c) a length of elastic cuff fabric, fixedly attached to the open bottom of said generally cylindrical body;
   d) a quantity of dry corn, placed within said cylinderical bag; and
   e) means for restricting the movement of said quantity of dry corn within said cylinderical bag.

* * * * *